Sept. 17, 1940. R. W. HAYGOOD Plant Pat. 422
SILVER-BLUE JUNIPERUS
Filed May 23, 1940
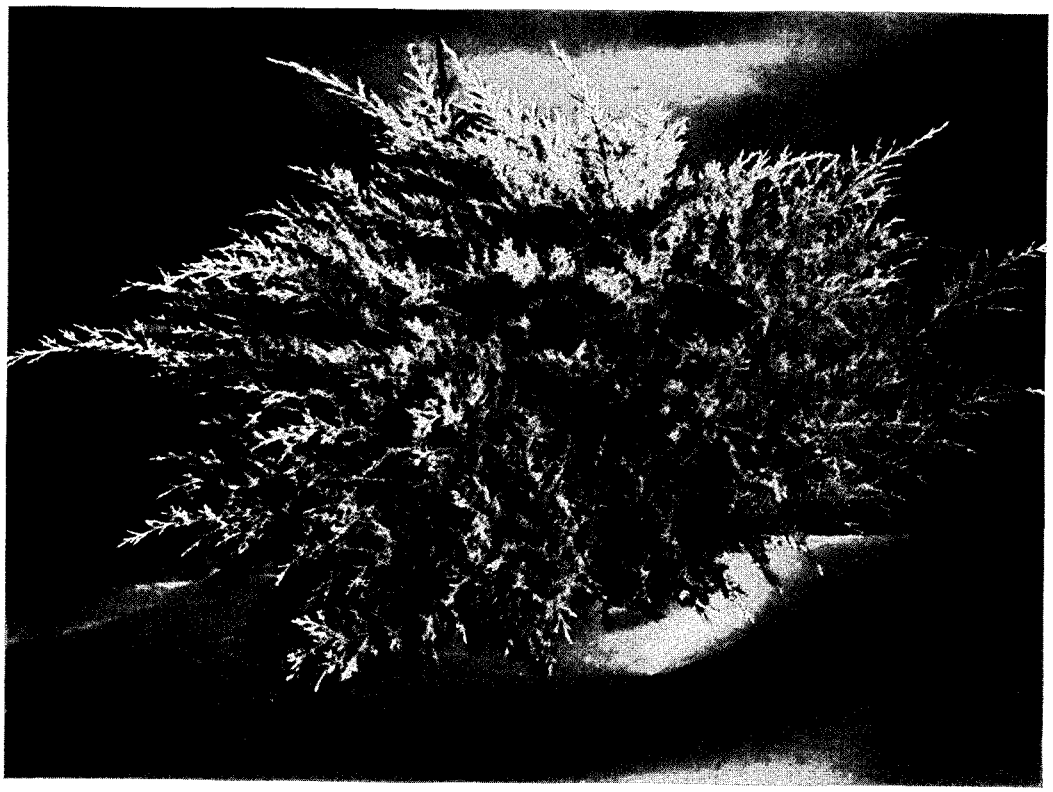
Inventor
Roger W. Haygood
By: Robb & Robb,
Attorneys Patented Sept. 17, 1940

Plant Pat. 422

UNITED STATES PATENT OFFICE

422

SILVER-BLUE JUNIPERUS

Roger W. Haygood, Keithville, La., assignor to
Texas Nursery Company, Sherman, Tex.

Application May 23, 1940, Serial No. 336,861

1 Claim. (Cl. 47—59)

My new variety of juniperus herein described was discovered in the prosecution of my work as a nurseryman and as a propagator of plants. The plant is of the genus Juniperus which I identify as belonging to the Chinensis species, and this plant is a new and distinct variety as it is entirely different in respect to its color as compared with any other *Juniperus chinensis* I, and others specializing in the propagation of junipers, have ever seen or have been able to find described by any botanist.

This new juniperus originated as a seedling, having been discovered among some seedling juniperus planted by me years ago. Since it requires several years for a juniperus plant to fully develop all of its characteristics, I have carefully observed this new variety of juniperus since its discovery and have asexually reproduced same by propagating it by means of grafts and cuttings, enabling me to ascertain that the novel characteristics of the plant as set forth herein, are fixed.

The plant is of upright, broad-spreading growth, showing both the needle-type and scale-type foliage, its distinct characteristic being its powdery silver-blue color which is maintained throughout the entire year.

This new juniperus has been grown by me under varied weather and soil conditions, and it has shown every characteristic of hardiness and adaptability that is true of *Juniperus chinensis*. It is adapted to many uses in landscape work and because of its silver-blue color it lends a variation to plantings not obtained by other plants of its type.

My new variety of juniperus herein described has every characteristic such as kind of foliage, nature of growth, form of plant, hardiness, thriftiness, etc., that is true of the variety known as *Juniperus chinensis pfitzeriana,* and in every way appears to be identical with *Juniperus chinensis pfitzerina,* with the exception that the foliage of this new juniperus is a powdery, silver-blue in color. The plant has held permanently its distinguishing characteristics through succeeding generations by means of asexual reproduction, as above stated. The propagation work performed by me was carried on by method of cuttings or grafts.

The following is a brief and detailed description of my new juniperus:

*Plant*—Upright, much branched, broad-spreading.

*Branches*—Horizontal, spreading, with nodding branchlets.

*Foliage*—Both needle-type and scale-type, and plume-like.

*Color of Foliage*—(Compared with Ridgeway Chart): powdery, silver-blue (Plate XLVII.)

*Growth*—Rapid and strong.

*Continuity*—Maintains distinctive color of silver-blue throughout year.

I claim:

A new and distinct variety of juniper plant, substantially as herein shown and described, characterized by the powdery silver-blue color of its foliage.

ROGER W. HAYGOOD.